US011783723B1

(12) United States Patent
Li

(10) Patent No.: US 11,783,723 B1
(45) Date of Patent: Oct. 10, 2023

(54) METHOD AND SYSTEM FOR MUSIC AND DANCE RECOMMENDATIONS

(71) Applicant: Dance4Healing Inc., Sunnyvale, CA (US)

(72) Inventor: Amy Chunmei Li, Sunnyvale, CA (US)

(73) Assignee: Dance4Healing Inc., Sunnyvale, CA (US)

( * ) Notice: Subject to any disclaimer, the term of this patent is extended or adjusted under 35 U.S.C. 154(b) by 368 days.

(21) Appl. No.: 16/900,883

(22) Filed: Jun. 13, 2020

Related U.S. Application Data

(60) Provisional application No. 62/860,957, filed on Jun. 13, 2019.

(51) Int. Cl.
| | |
|---|---|
| *G09B 19/00* | (2006.01) |
| *G06Q 50/00* | (2012.01) |
| *G16H 20/30* | (2018.01) |
| *G16H 50/20* | (2018.01) |
| *A61B 5/16* | (2006.01) |
| *G06N 20/00* | (2019.01) |
| *G09B 5/06* | (2006.01) |
| *G06N 5/04* | (2023.01) |

(52) U.S. Cl.
CPC .......... *G09B 19/0015* (2013.01); *A61B 5/165* (2013.01); *A61B 5/167* (2013.01); *G06N 5/04* (2013.01); *G06N 20/00* (2019.01); *G06Q 50/01* (2013.01); *G09B 5/065* (2013.01); *G16H 20/30* (2018.01); *G16H 50/20* (2018.01)

(58) Field of Classification Search
CPC .... G09B 19/0015; G09B 5/065; G16H 20/30; G16H 50/20; G06N 20/00; G06N 5/04; A61B 5/165; A61B 5/167; G06Q 50/01
See application file for complete search history.

(56) References Cited

U.S. PATENT DOCUMENTS

| | | | | |
|---|---|---|---|---|
| 5,830,107 | A | * 11/1998 | Brigliadoro | A63B 23/03575 482/3 |
| 6,227,968 | B1 | 5/2001 | Suzuki et al. | |
| 6,410,835 | B2 | 6/2002 | Suzuki et al. | |
| 6,782,308 | B2 | 8/2004 | Yamaura | |
| 8,057,290 | B2 | 11/2011 | Vance et al. | |
| 8,260,778 | B2 | 9/2012 | Ghatak | |
| 8,326,584 | B1 | 12/2012 | Wells et al. | |
| 8,444,464 | B2 | 5/2013 | Boch et al. | |
| D689,902 | S | 9/2013 | Carriuolo et al. | |
| D689,905 | S | 9/2013 | Moriya et al. | |
| 8,562,403 | B2 | 10/2013 | Boch et al. | |
| 10,086,283 | B2 * | 10/2018 | Trewartha | A63F 13/211 |

(Continued)

*Primary Examiner* — Malina D. Blaise
(74) *Attorney, Agent, or Firm* — Duane Morris LLP; Thomas J. Kowalski; Deborah L. Lu

(57) ABSTRACT

A method and system that includes at least one processor, the at least one computer in communication with at least one data storage unit, the at least one computer programmed and/or configured to: generate a plurality of dance sequences; associate or cause the association of each of the plurality of dance sequences with at least one dance corpus classification; generate, for each of the plurality of users, a user profile; receive, from each of the plurality of users, at least one preference data; associate or causing the association of each of the user's profile with at least one preference data; and generate a recommendation of a dance sequence for each of the plurality of users.

20 Claims, 13 Drawing Sheets

(56) References Cited

U.S. PATENT DOCUMENTS

| | | | |
|---|---|---|---|
| 10,268,808 B2* | 4/2019 | Lyske | G06F 21/10 |
| 11,657,553 B2* | 5/2023 | Troutman | G06T 11/60 |
| | | | 345/619 |
| 2002/0019258 A1* | 2/2002 | Kim | A63F 13/5375 |
| | | | 463/36 |
| 2006/0266200 A1* | 11/2006 | Goodwin | A63F 13/424 |
| | | | 84/611 |
| 2008/0234023 A1* | 9/2008 | Mullahkhel | A63F 13/211 |
| | | | 463/7 |
| 2010/0022287 A1 | 1/2010 | Chiwata | |
| 2010/0041454 A1 | 2/2010 | Huang | |
| 2010/0045609 A1* | 2/2010 | Do | G06F 3/011 |
| | | | 345/173 |
| 2010/0113117 A1 | 5/2010 | Ku et al. | |
| 2011/0040707 A1 | 2/2011 | Theisen et al. | |
| 2011/0306396 A1 | 12/2011 | Flury et al. | |
| 2012/0088216 A1* | 4/2012 | Wexler | G09B 5/00 |
| | | | 434/322 |
| 2012/0094730 A1 | 4/2012 | Egozy | |
| 2012/0143358 A1* | 6/2012 | Adams | G06F 3/0482 |
| | | | 700/92 |
| 2012/0151344 A1* | 6/2012 | Humphrey | G09B 19/0015 |
| | | | 715/716 |
| 2014/0070957 A1* | 3/2014 | Longinotti-Buitoni | |
| | | | A61B 5/02055 |
| | | | 340/870.01 |
| 2016/0216130 A1* | 7/2016 | Abramson | G01C 21/3423 |
| 2017/0259120 A1* | 9/2017 | King | H04L 67/306 |
| 2017/0263147 A1* | 9/2017 | King | G11B 27/026 |
| 2018/0012389 A1* | 1/2018 | Kishi | G10H 1/00 |
| 2018/0025004 A1* | 1/2018 | Koenig | H04L 67/306 |
| | | | 715/748 |
| 2018/0036591 A1* | 2/2018 | King | H04N 5/76 |
| 2018/0181730 A1* | 6/2018 | Lyske | G11B 20/00891 |
| 2018/0214777 A1* | 8/2018 | Hingorani | A63F 13/5255 |
| 2019/0049968 A1* | 2/2019 | Dean | A61G 5/04 |
| 2019/0122577 A1* | 4/2019 | Mora | G09B 5/06 |
| 2019/0240539 A1* | 8/2019 | Perlman | H04N 21/26258 |
| 2020/0286505 A1* | 9/2020 | Osborne | G06N 3/08 |
| 2020/0342646 A1* | 10/2020 | Wang | G06N 3/045 |

* cited by examiner

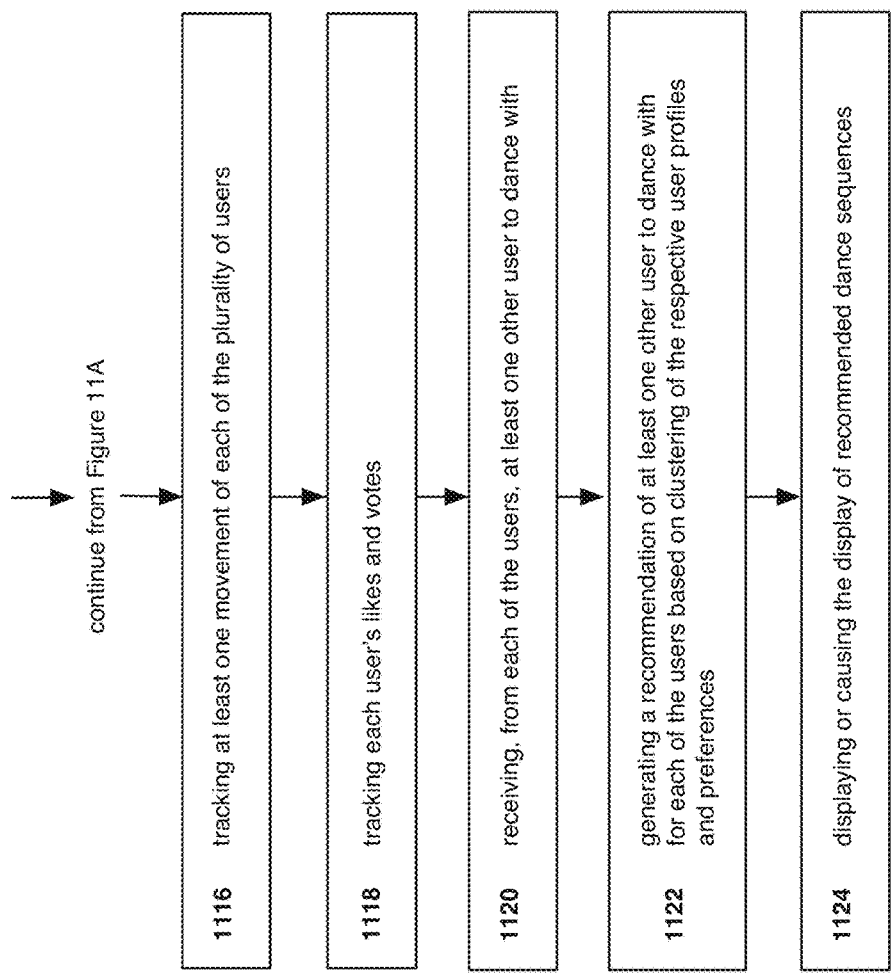

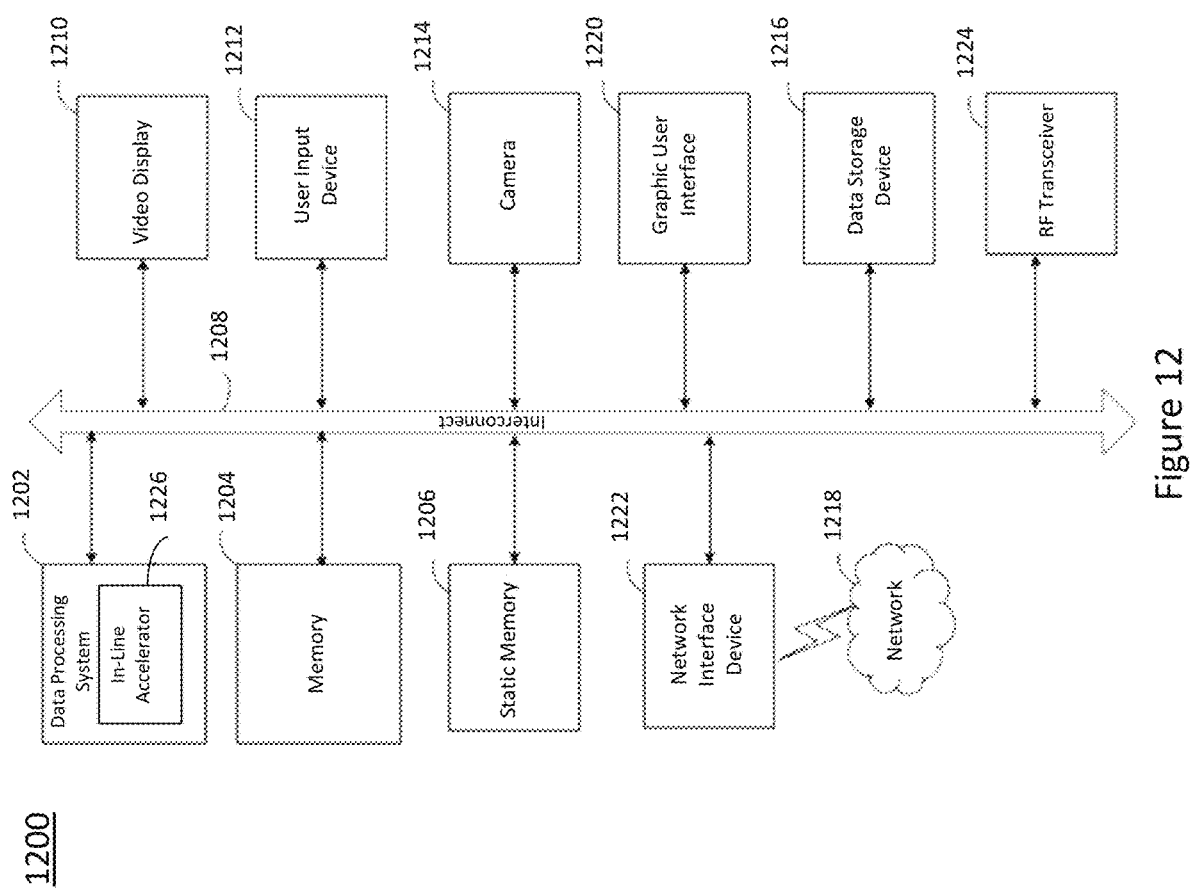

METHOD AND SYSTEM FOR MUSIC AND DANCE RECOMMENDATIONS

FIELD OF THE INVENTION

The invention relates generally to a method and system for providing users with personalized recommendations for music and dance.

BACKGROUND OF THE INVENTION

Behavior change is a big challenge in the healthcare industry. Research has shown that many health impaired people know the benefits of exercise but don't do it, because even though they have both the ability and motivation for exercise, they do not have a "trigger"—a reason to shift into an exercise mode. Music, used for centuries to reduce stress and anxiety, is also a natural trigger for dance.

SUMMARY OF THE INVENTION

In one embodiment, the present design provides a method and system for providing users with personalized recommendations for music and dance. Generally, provided is an improved method and system for recommending dance sequences based on user preferences and other data, tailored to their needs.

According to one embodiment, provided is a computer-implemented method for providing a plurality of users with an environment for personalized dance activities, the method comprising: generating a plurality of dance sequences; associating or causing the association of each of the plurality of dance sequences with at least one dance corpus classification; generating, for each of the plurality of users, a user profile; receiving, from each of the plurality of users, at least one preference data; associating or causing the association of each of the user's profile with the at least one preference data; and generating a recommendation of a dance sequence for each of the plurality of users.

According to another embodiment, provided is a system for providing a plurality of users with an environment for personalized dance activities, the system comprising: at least one computer including at least one processor, the at least one computer in communication with at least one data storage unit, the at least one computer programmed and/or configured to: generate a plurality of dance sequences; associate or cause the association of each of the plurality of dance sequences with at least one dance corpus classification; generate, for each of the plurality of users, a user profile; receive, from each of the plurality of users, at least one preference data; associate or cause the association of each of the user's profile with the at least one preference data; and generate a recommendation of a dance sequence for each of the plurality of users.

BRIEF DESCRIPTION OF THE DRAWINGS

FIG. 12 is a diagram of a computer system including a data processing system according to an embodiment of the invention.

DETAILED DESCRIPTION

Figure 1:
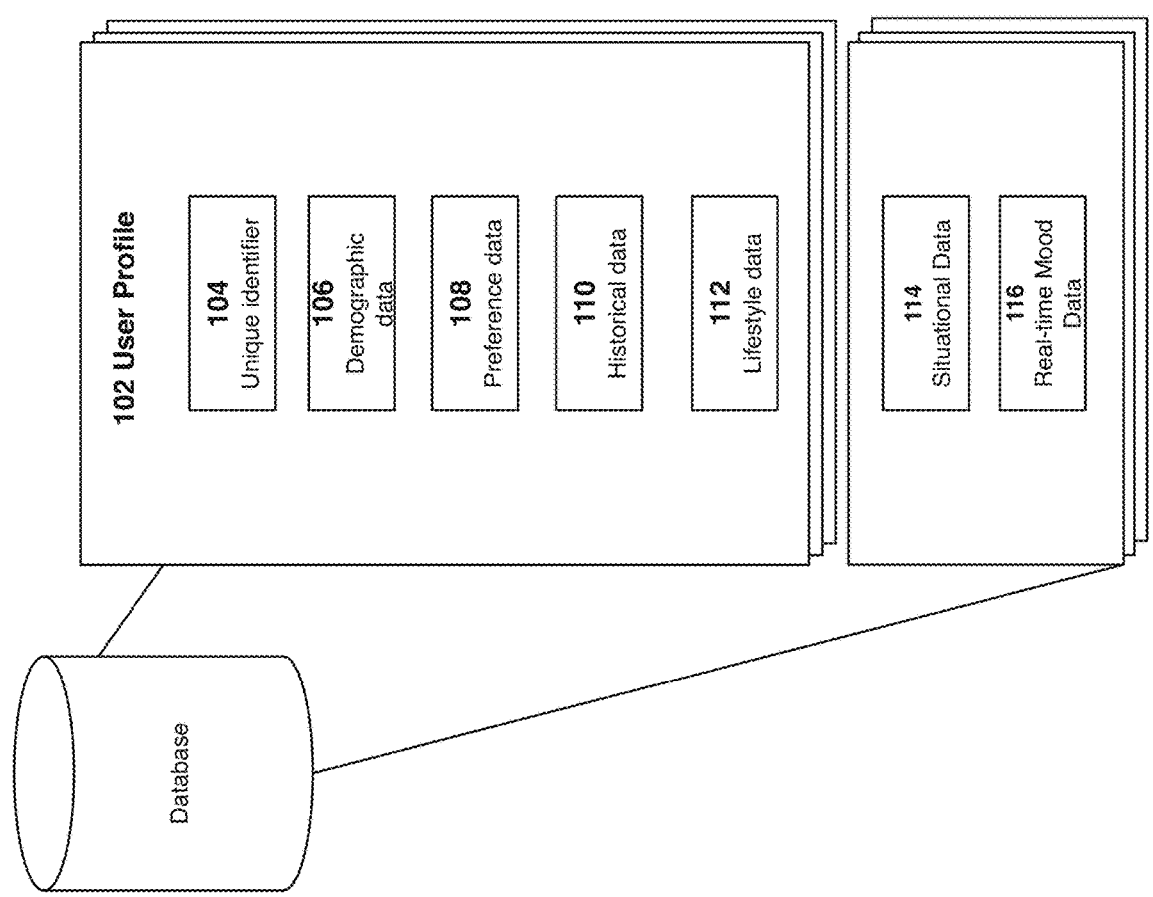
FIG. 1 is a block diagram of a user profile database according to the principles of the present invention.

In various embodiments, described in enabling detail below, the invention provides an ecosystem comprised of applications, a community-building platform, hardware sensors, and peripheral components, to quantify, analyze, and interpret both physiological biometric data and mood data in a manner that enables the user to engage in dance as a healing modality.

According to the American Psychological Association 2017 report, 75 percent of Americans experienced at least one symptom of acute stress in the month prior to the survey. More specifically, about one-third of adults said they had experienced feeling nervous or anxious (36 percent), irritability or anger (35 percent), and fatigue (34 percent) as a result of their stress levels. Published medical studies reveal dance will improve both physical and emotional well-being, and provide substantial neurological benefits, for example, dancing frequently reduces the risk of dementia by 76%, cardiovascular death by 46%. Dance/movement therapy, especially synchronized movement to rhythm, is highly effective not only for physical well-being, but more importantly, for emotional well-being. Dance/movement therapy is more broadly effective than physical therapy and other exercises; dance increases oxytocin, serotonin, and decreases dopamine, giving you a more euthymic brain. Hand/finger dances/exercises help people with restricted movements by promoting neuroplasticity in the brain, increasing motor skills, brain synapsing efficiency, balance, coordination, and timing.

There are prior approaches for artificial intelligence and recommendation systems for related applications. Music recommendation systems are based on four broad categories of inputs for their recommendations: (1) metadata such as genre, album, artist, etc (2) acoustic terms such as rhythm, beats, melody, etc.; (3) direct feedback from the users such as a rating of mood, likes, dislikes, biometrics etc.; and (4) collaborative feedback such as information listening patterns. Current music recommendations use the four inputs above in a weighted system to make a recommendation. There is a prior approach for personalized exercise programs, but it does not consider dance to be an exercise to recommend. There is a prior approach to recognize when a person is dancing, but it is not used for recommendations. No system exists for recommending music and dance. No such system exists for recommending dance.

Moreover, unlike music, dance introduces physical requirements. Currently there is no system that recommends dance based on mood and/or physical condition. Technology can track dance moves using skeletal sensors or computer vision. However, there is no system of personalized recommendation of dance based on gathering data from skeletal tracking, health conditions, and moods. In different embodiments, the present design has roots in neuroscience and uses artificial intelligence to recommend music, dance styles, and peer groups based on emotion, health conditions, and energy levels. In some embodiments, the behavior design and gamification are used to encourage learning while building dance habits. The system in one embodiment includes at-home training with movement feedback, "mobile on the go" to continue the healing process throughout the day, and a platform to build a community focused on music and dance for healing. The present design also empowers participants to sync live with their communities, as if they were dancing to the same music even though they are not at the same location.

Contextualized data tracking reveals how music and movement can improve physiological functions and help achieve a more euthymic state.

FIG. 1 is a block diagram of one embodiment of the system's database 100, including one or more user profiles 102. In one embodiment, each user profile includes one or more of the attributes. For example, such attributes include:

Unique user identifier 104, which includes, but is not limited to the user's email address, phone number or other form of a unique identifier;

Demographic data 106, which for example includes age, gender, genetics, ethnicity, weight, height, occupation, residential city, socioeconomic status;

Preference data 108, which for example includes privacy preference; energy level, favorite music, dance, singers, dancers, dance teachers, and groups; hobbies and interests; individuals/teachers/groups that he/she follows, and technical capability (low, medium, advanced); availability to dance (weekly schedule, preferences);

Historical data 110, which for example includes health condition, history (date of diagnosis, type of disease, area of the body, type of surgery, type of treatment), orthopedic as well as musculoskeletal problems, exercise habits (activity, frequency, duration), physiological measurements by sensors during exercise; and Lifestyle data 112, which, for example, is also tracked to gauge users' stress level and general wellbeing. This data includes: sleep, personality, romantic activity, sexual activity, diet, activities that require neurological executive planning and execution, how often a user goes to the gym, frequency and quality of family contact, community activities (call log, text, message, social media activities, family activities, and events). Social interaction and community support are utilized for data tracking as well. For example, friends and families can report a person's emotional states and wellness (buddy system).

With continued reference to FIG. 1, in one embodiment, real-time situational data 114 is also collected. Such data includes one or more of the following: current medication effects, time, geographic location, device used (mobile, web, TV), and browser. Other external data may also be tracked to reveal the impact of users' emotions, such as social media, weather events, social and political climate, natural disasters, public health crises, pandemics, economic volatility and inequities, as well as other local, national and global events, such as, recent protests against racism across the globe.

With further reference to FIG. 1, in another embodiment, the user's real-time mood data 116 is also collected. The mood can include, such as but not limited to, happy, sad, tired, worried, scared, and angry. The mood tracking can be achieved both through self-report data within the user interface as well as computer vision and facial recognition technology.

Figure 2:
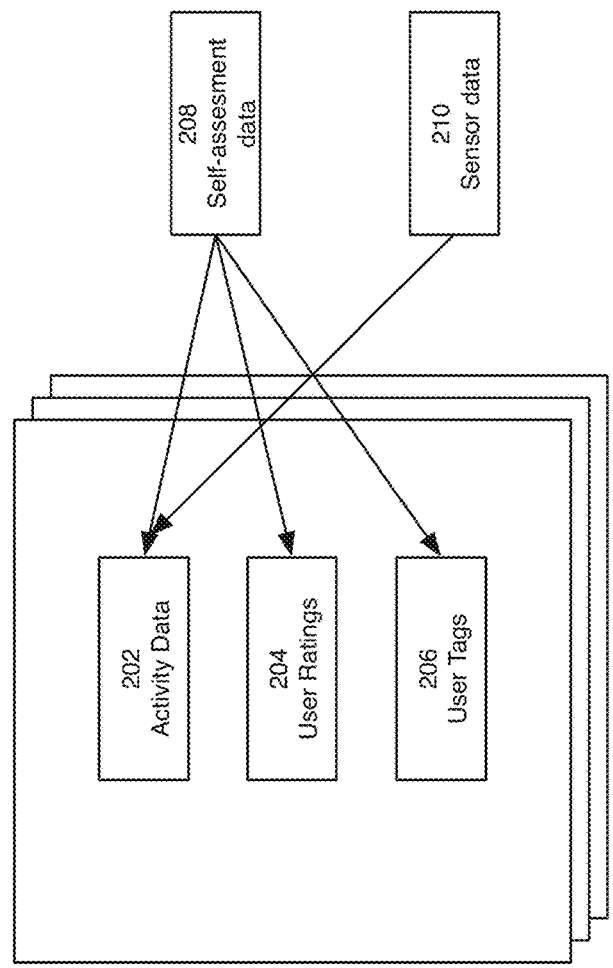
FIG. 2 is a block diagram of a user activity profile database according to the principles of the present invention.

FIG. 2 is a block diagram according to one embodiment of the system's database 200. The database 200 includes, for example, but not limited to, tracking information. The tracking information includes, for example, one or more of the following: activity data 202, user ratings 204 and user tags 206.

With continued reference to FIG. 2, activity data 202 tracks emotions before, during and after the dance, music (song title, genre, major key, minor key, etc.), dance (style, speed, intensity, energy level, upper body, lower body, etc.), duration of dance, calories burned, physiological progress measurements, what triggers the person to dance (music, reminders, events, buddy support), what causes the participant to continue dancing, and associated metrics. This data shows the user the impact of dance movement on their emotional state and physiological health. The activity data 202 in one embodiment has at least two general categories, and can be expanded to accommodate or enable new capabilities and features. The two categories may include but are not limited to:

a) self-assessment data 208 includes but not limited to multiple facets of well-being; physical, social/family, emotional, functional, plus additional concerns in questionnaire format ; and b) sensor data 210 includes camera tracking and sensors (including but not limited to skeletal tracking and wearable devices) to gather information from different biosignals. The types of biosignals include, but are not limited to, heart rate, heart rate variability (HRV), musculoskeletal movement, speech recognition and speech analysis, respiratory patterns, oxygenation measurements, body temperature, blood pressure, electrodermal (galvanic skin) response as well as electrical conduction measurements, and electrical brain measurements. In one embodiment, biosignals are analyzed using standard algorithms that interpret the data and determine a user's physiological state, mood, and including but not limited to stress levels.

With continued reference to FIG. 2, user ratings 204 may include, for example, but not limited to, votes, frequency of use, user reviews, favorites, and saved dance sessions, videos, and sequences.

With further reference to FIG. 2, user tags 206 are different classifications made by the users and inputted into the system, such as 'jazz', 'beginners', 'happy', 'slow', etc. In one embodiment, user tags 206 may be programmatically added by applying standard music analysis techniques.

Figure 3:
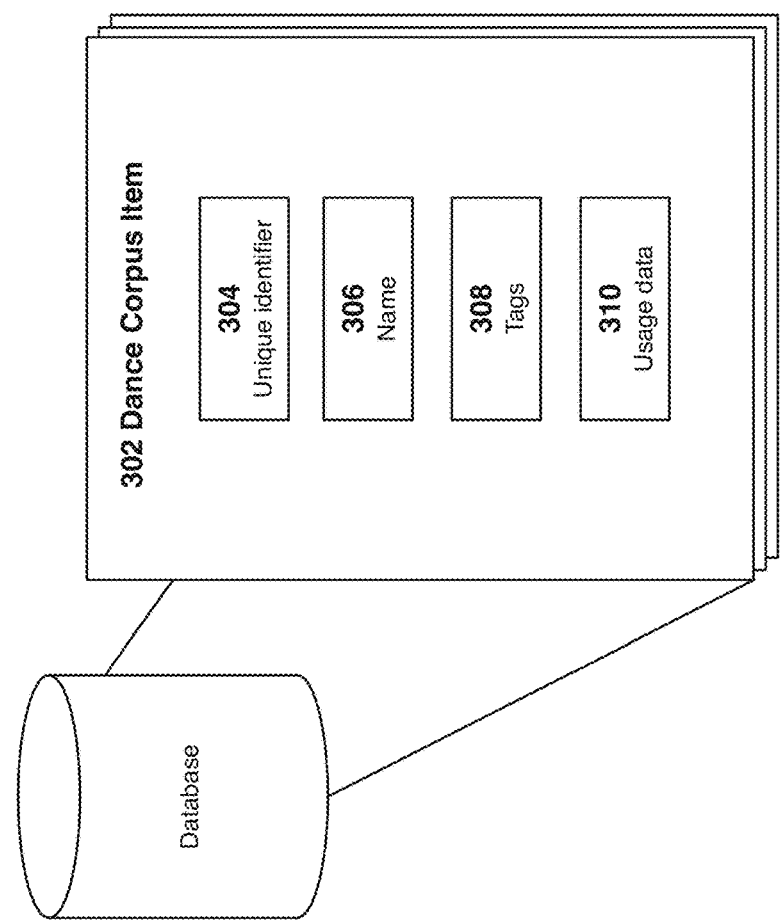
FIG. 3 is a block diagram of a dance corpus database according to the principles of the present invention.

FIG. 3 is a block diagram according to one embodiment of the system's database 300 including dance corpus item 302. Each user profile includes one or more of the following attributes: unique identifier 304, name 306 of song or dance, tags 308 (e.g. slow, fast, hip-hop), and usage data 310 (e.g. how many times the dance corpus being played, frequency, whether user finishes the dance sequence, etc.).

With continued reference to FIG. 3, unique user identifier 304, which for example includes, but not limited to the user's email address, phone number, or other forms of unique identifiers.

Figure 4:
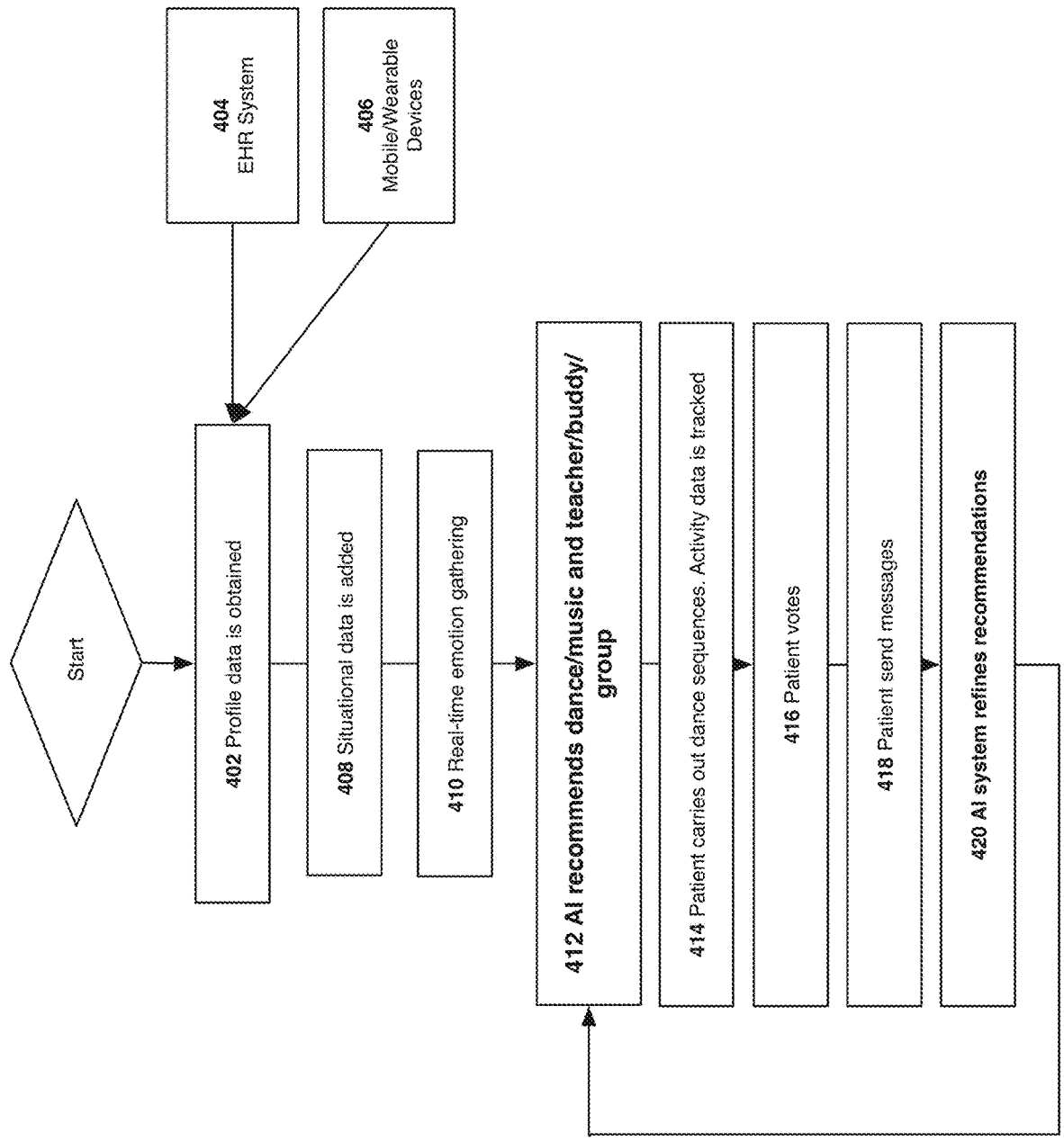
FIG. 4 is a flow chart of a system workflow according to the principles of the present invention.

FIG. 4 is a flow chart according to one embodiment of a workflow 400 of a system (e.g., system 800, system 1200) for providing personalized recommendations for music and dance based on the profile, situational, lifestyle and activity data. According to one embodiment, data acquisition is performed by asking the user to fill out a web form or a mobile application form at operation 402. According to another embodiment, such data may be added automatically by interfacing with an EHR system APIs 404 (e.g., AllScripts, Epic, etc.), or mobile, wearable or medical device SDK 406 (e.g., GPS location and wearable device logs). According to another embodiment, the user is asked for his or her situational data at operation 408 which may include one or more of the following: his or her schedule or availability data, behavioral triggers (e.g., reminders, notification due to insufficient physical activity), energy level, desired dance duration, whether they would like to dance alone or with a buddy/group. According to a further embodiment, the user is asked for his or her current mood 410 (e.g. happy or sad), this mood data can be gathered through self-report data via clinical surveys, an interface of a telehealth platform, as well as technology like facial recognition, computer vision, etc.

With continued reference to FIG. 4, the user is presented with videos of different dance routines matching his or her profile and situational data at operation 412, as described hereinbelow. In one embodiment, the system will recommend different dance teachers, dance buddies, or dance groups as described hereinbelow. The user can then choose a specific dance routine associated with such teachers, buddies, or groups. Once a dance routine is selected, the dance video from the system's video repository is presented to the user. As the user executes the dance sequence, tracking information is collected as described hereinbelow at operation 414. According to one embodiment, standard skeletal tracker, thermal tracking, oxygenation circulatory tracking, biosensor, wearable device, smart garment, camera, accelerometer or other methods are used to evaluate a user's dance sequence and progress (for example, is the user capable of following the music's beat, or the dance instructions). According to another embodiment, human motion is captured and matched against the music using standard methods, such as beat extraction or by inputting music beat information directly, and comparing that to change of motion at critical timing (as implemented by systems such as Kinect). Before, during, or after the execution of the dance, the user may provide feedback at operation 416 (e.g., upvote, downvote, favorite, save to list, etc.). Such data is stored in the user's profile and in the dance database. According to a further embodiment, the system allows the user to send messages (such as encouragement, recommendations, etc.) including, but not limited to, video, audio, olfactory/smell, virtual reality, and text to their groups and friends at operation 418. Finally, the system uses the new data to refine its recommendations going forward at operation 420 as described hereinbelow. According to one embodiment, the refinement can be done through online learning machine algorithm methodologies such as stochastic gradient descent which result in adjusted recommendations to each patient based on his/her most recent activities.

Figure 5:
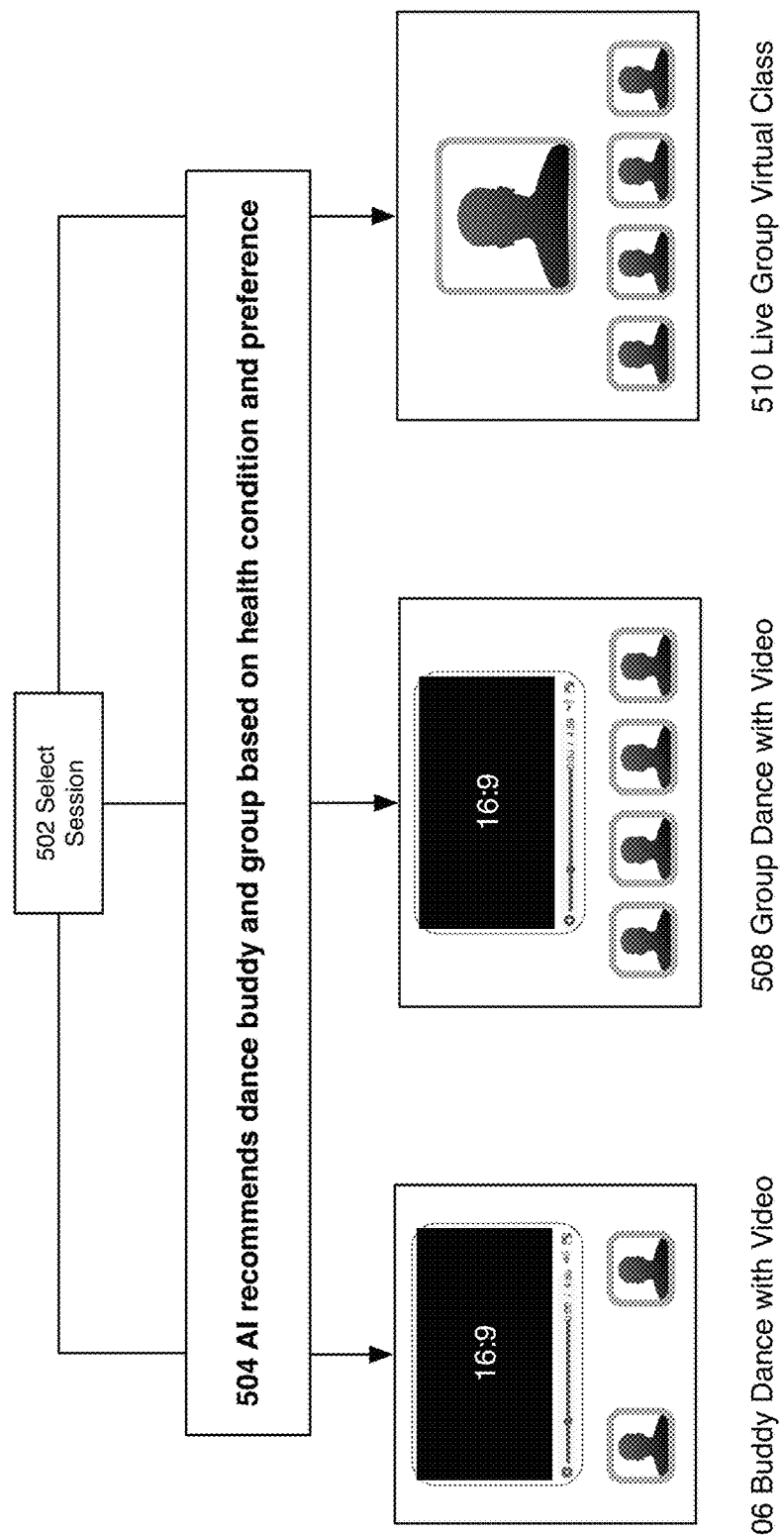
FIG. 5 is a block diagram of a system display modes according to the principles of the present invention.

FIG. 5 is a block diagram of one embodiment of the system's different display modes. According to one embodiment, the user selects a session at operation 502. At operation 504, AI recommends dance buddies and groups based on health condition, personality type, energy level, capability, and preference. In one embodiment, there are different types of sessions to select from: a session based on a pre-recorded dance sequence; in such case, the AI engine will recommend one or more video sequences and the user will select one; a "buddy" to dance with. The AI engine will recommend one or more "buddies" for the user to choose from. Once both users have agreed to be accountable buddies, the users will then be presented with a side-by-side video view, whereas both users can view each other's dance moves while watching the same pre-recorded videos, sessions, sequences; a group dance with the same video sequences, or live video teaching classes, where the AI engine will recommend one or more groups for the user to choose from and then display all users video streams in that particular group.

With continued reference to FIG. 5, 506 refers to sessions having buddy dance with video, 508 refers to sessions having group dance with video, 510 refers to live group virtual class.

Figure 6:
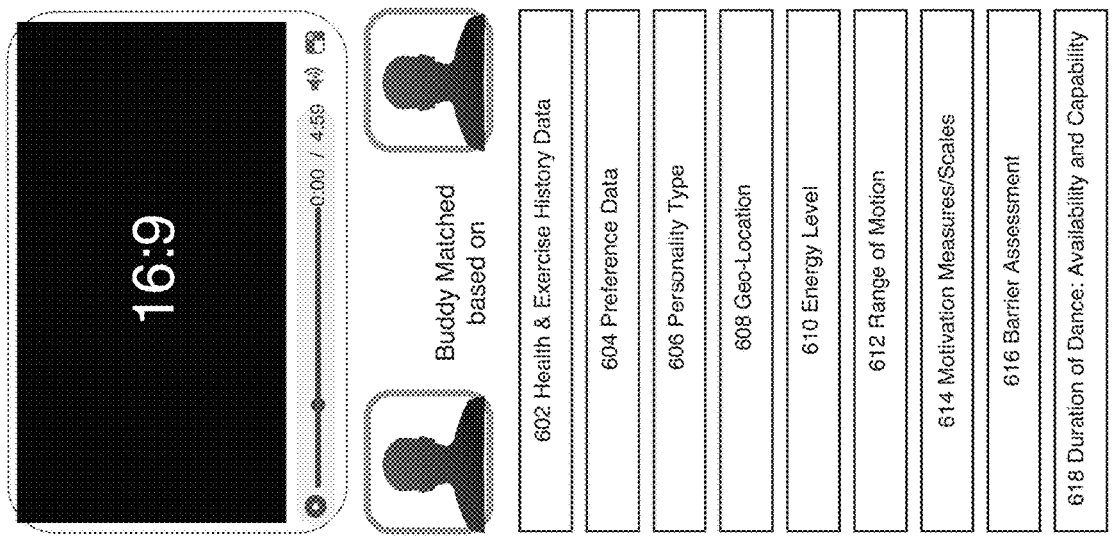
FIG. 6 is a block diagram of a system network and devices according to the principles of the present invention.

FIG. 6 illustrates how an AI engine recommends a committed behavior change buddy based on modules or functions including patient's Health and Exercise History data 602, Preference data 604, and Personality Type 606. Geolocation 608 will also be considered if users have indicated interest to meet their committed buddy not only online, but also in person. Our AI matching algorithm will focus on matching buddies based on their Energy Level 601, Range of Motion 612, Motivation Measures/Scales 614, Barrier Assessment 616, Duration of dance: Availability and Capability 618. Energy level has been validated by our users as one of the most important factors for them to be able to enjoy exercises and movements with a buddy. The availability and capability for the duration of dance is also an important factor to make the matching buddy easier to accommodate each other's schedule and time. Research has also shown different personality types create different preferences for exercise, music, and dance. This preference is important as they are crucial for an individual's comfort level, engagement, and commitment to the exercise activities. For example, a more mathematical engineer type of personality may prefer exercises and dances that are more structured, while a more artistic, creative type of personality may prefer more freeform types of exercises or dances. Below are some examples included, but not limited to on how we plan to match buddies based on personality types. There are traditional personality matching for compatibility. There are also multiple personality matching API. In one example, the present design utilizes a personality API which tracks individuals' social media activities, and analyzes their data to provide a personality recommendation.

Figure 7:
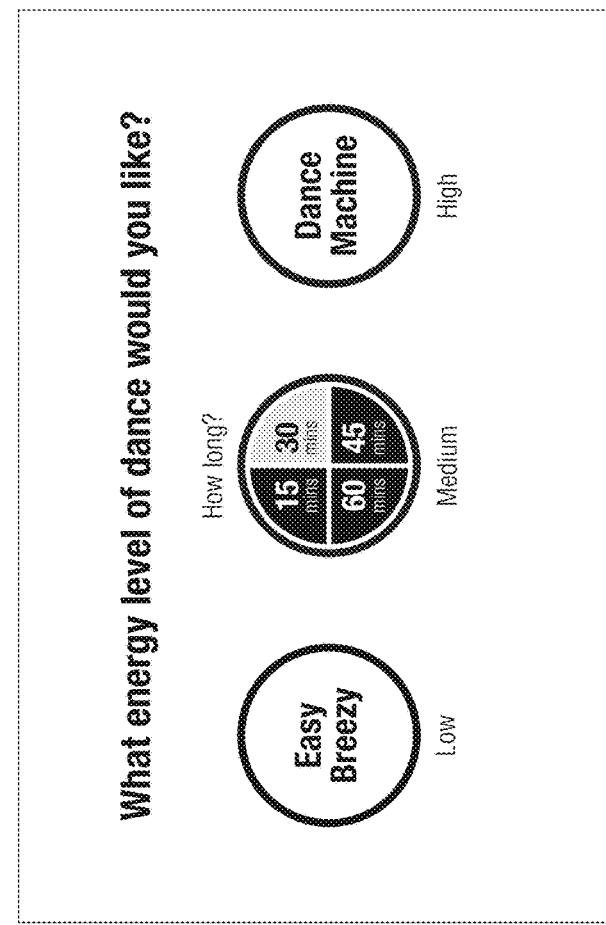
FIG. 7 illustrates examples of user interfaces provided by a platform of the present design.
Figure 7:
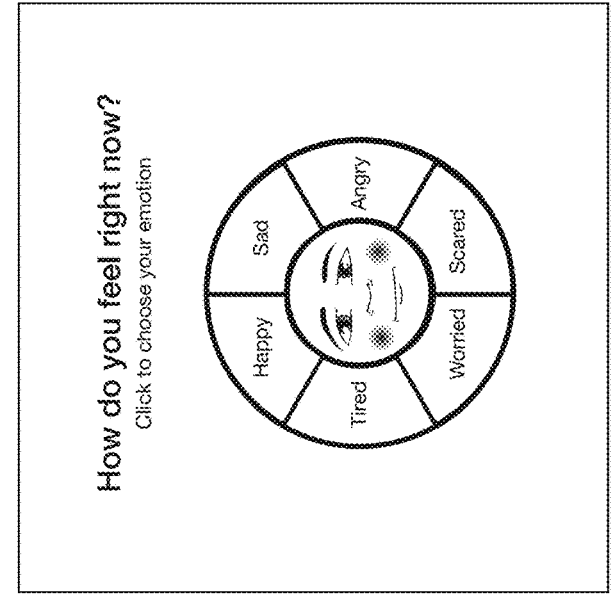

FIG. 7 illustrates examples of user interfaces provided by a platform of the present design. As participants log in to the platform (e.g., dance healing platform, telehealth platform), this platform asks for their self-reported emotion, energy levels, and duration of the dance. User interface 701 shows the emotions to choose from including happy, sad, tired, angry, worried, and scared. These emotions can be customized based on the group of users we will be serving and the recommendation of their physicians and therapists. User interface 702 illustrates the energy levels to select from: low (Easy Breezy), medium (Mellow Bellow), and high (Dance Machine). The capability is reported as the length of time to dance which is selected from: 15 minutes, 30 minutes, 45 minutes, and 60 minutes. After the dance class, the emotion is reported again to track the before and after to use as a factor in future recommendations. Computer vision and facial recognition technology will be used as well for facial emotion tracking, the tracking data will be compared to participants' self-report data to ensure and improve the accuracy of the data.

Figure 8:
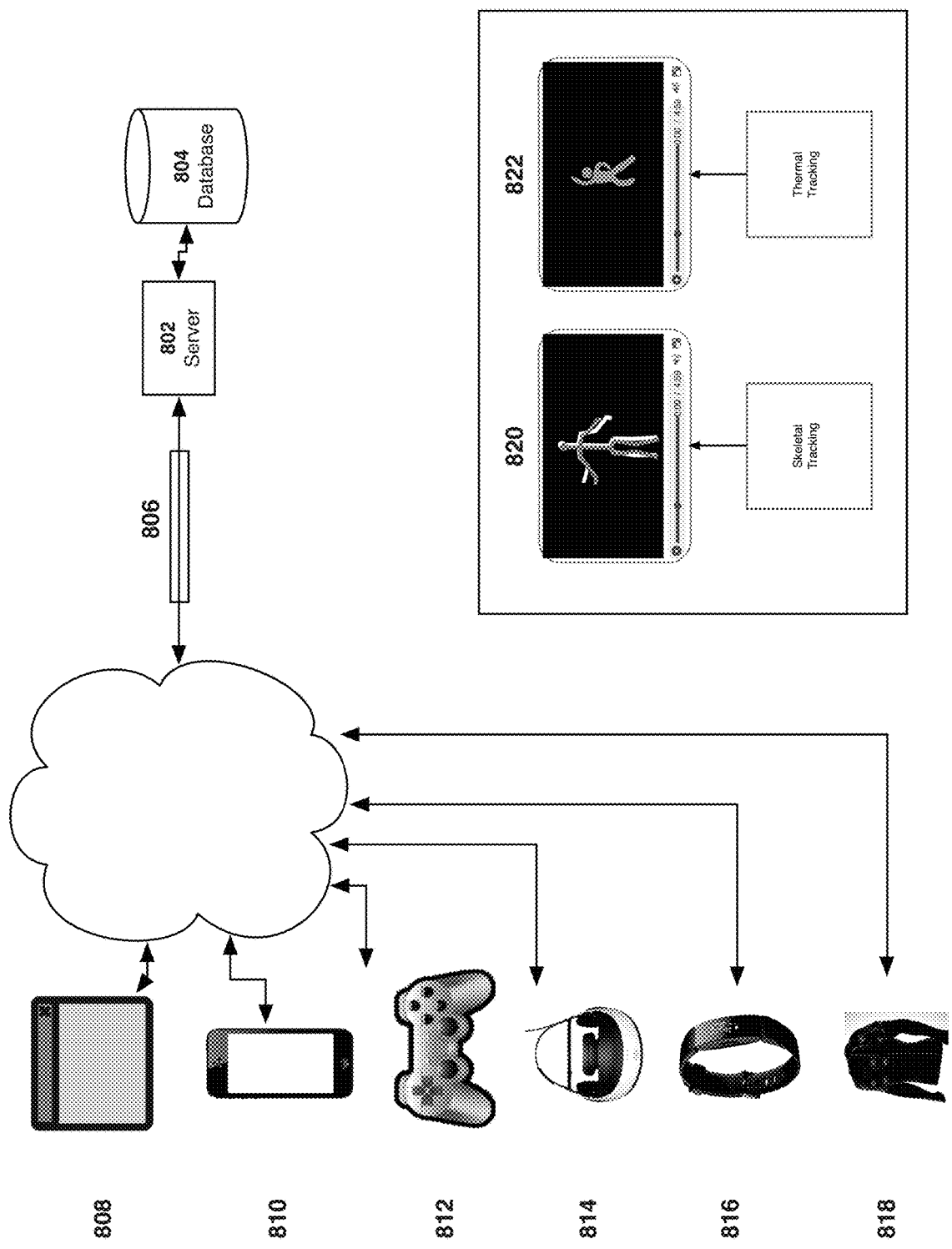
FIG. 8 is a block diagram of one embodiment of a network architecture of a system 800.

FIG. 8 is a block diagram of one embodiment of a network architecture of a system 800. According to one embodiment, the system 800 includes a server 802, a database 804 (e.g., SQL or NoSQL databases), connected over a network 806 (e.g., the Internet, cellular) to, for example, a user's web browser 808, mobile device 810, controller 812, other network device 814, wearable device 816, and smart garment 818. The communication uses standard internet protocols such as HTTP or HTTPS, as well as WebRTC or H323 and other streaming protocols for transferring of video and sound. The database 804 stores the users' profile information, user activity profiles, and the music and dance corpus.

With continued reference to FIG. 8, according to one embodiment, user actions and streamed content are logged and stored in the database 804 where it can later be retrieved to generate unique recommendations for the user. Each user's video usage data (which video, frequency, finish or not) is captured at his or her device such as web browser 808, mobile device 810, streamed to the server 802 and the server then multiplexes the streams and communicates them to the respective end user's devices.

With continued reference to FIG. 8, according to another embodiment, the system also includes controller 812, such as a PlayStation or Xbox controller, specialized remote control, or other hardware. Users are able to use the controller to enter profile data, provide feedback (thumbs up, thumbs down, favorite, save dance), select which type class/program/package they want to enroll in, etc. In one embodiment, the interface includes a virtual reality device 814, which is connected to the server system. Such a device can be used to consume the video stream from the server. In one embodiment, the interface includes wearable devices 816 and smart garment 818 that can track different biosignals, such as, but not limited to, heart rate, heart rate variability, steps, oxygenation measurement, etc. When such devices are used, the built-in tracking mechanism from these devices will also be engaged to further track user's usage data, progress, and feedback.

With continued reference to FIG. 8, as the user executes the dance sequence, tracking information is collected. According to one embodiment, standard skeletal tracker, thermal tracking, oxygenation circulatory tracking, biosensor, wearable device, smart garment, camera, accelerometer and/or other methods are used to evaluate a user's dance sequence and progress (for example, is the user capable of following the music's beat, or the dance instructions). According to another embodiment, human motion is captured and matched against the music using standard methods, such as beat extraction or by inputting music beat information directly, and comparing that to change of motion at critical timing (as implemented by systems such as Kinect). According to one embodiment, skeletal tracker 820 can also be expanded from one skeletal tracking to track user to creating a second skeletal tracking to track the instructor in the recorded instructional videos. As the user dances with the instructor video, if the user's skeleton is matching the instructor's skeleton, it communicates that the user is doing the correct movement/dance. This will allow us to further access the accuracy and the effectiveness of users' movement. Such implementation can also be expanded from dance movements tracking to physical therapy, occupational therapy, and sports medicine tracking. According to another embodiment, thermal tracking 822 will also be utilized to monitor the body temperature and possible circulatory issues (e.g. peripheral vascular disorders) of the users. When such devices are used, the built-in tracking mechanism from these devices will also be engaged to further track user's usage data, progress, and feedback.

With further reference to FIG. 8, the recommendation process is meant to recommend a video that is appropriate according to the user's profile, overall collected tracking data and real-time emotion. These recommendations are obtained via information gathered from following user activity, physiological progress, or via explicit feedback or categorization by users who share a similar affinity of music and dance, similar demographic profile, geo-location, as well as others who share similar health conditions. For example, a 48-year-old breast cancer patient with limited upper body movement due to a mastectomy and a preference for a certain music and dance genre reporting a certain type of emotion, will be matched with music and dance that have been proven beneficial to other patients with similar conditions, restrictions and preferences, and who had reported similar real-time emotions. The recommendation process will also further tracking users' usage data, progress, and feedback to improve safety protocols to users, and groups of users with similar conditions or preferences.

Figure 9:
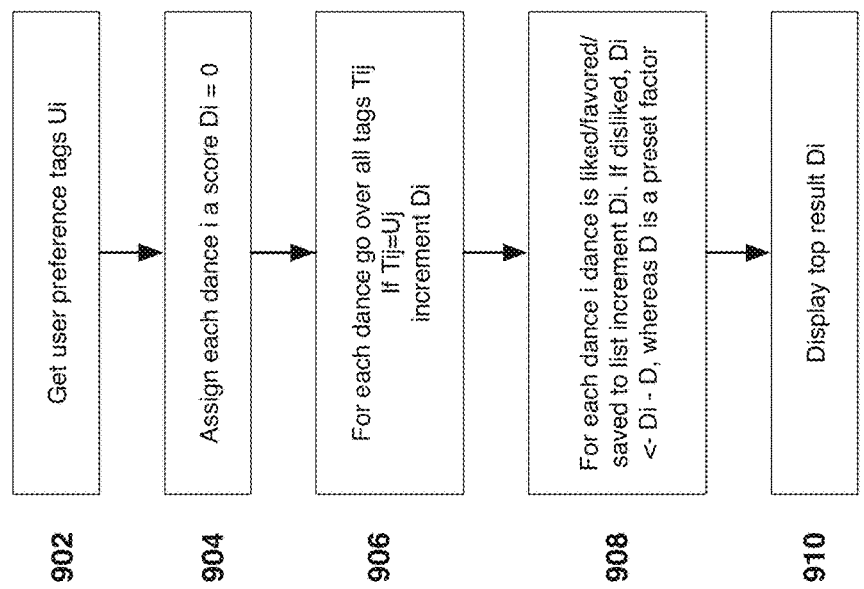
FIG. 9 is a block diagram of a dance recommendation engine according to the principles of the present invention.

FIG. 9 is a flow chart of operations for one embodiment of the system's recommendation engine 900 with the matching of music and dance based on explicit attributes or tags associated with each music and dance (e.g., jazz, hip-hop, suitable for seniors, suitable for people with limited upper body movement and energy level). According to one embodiment, the match is obtained by matching the user profile against all dance routines and calculating the matching score based on these tags. For example, tags indicated by the user are obtained at operation 902, and each dance is assigned a score of zero at operation 904 that is incremented for each matching tag at operation 906. According to another embodiment, specific user feedback pertaining to the dance, such as an up-vote, like or save for later causes the score to increase, and a dislike decreases it by a predefined factor, typically large enough to lower the probability of such a dance being suggested by the system at operation 908. The top matching dances are displayed at operation 910.

With continued reference to FIG. 9, making personal recommendations makes use of deep learning, or any other type of artificial intelligence, such as collaborative filtering, a social system which bases its recommendation on the judgment or feedback of a large number of people, to recommend music and dance that proved beneficial for similar patients with similar profiles, preferences, activity profile, and mood. Such collaborative filtering methods may rely on simple item-to-item filtering, based on the user profile and the dance attributes. The user then receives the top results ranked by standard distance metrics such as cosine distance.

With continued reference to FIG. 9, according to one embodiment, Probabilistic Latent Semantic Analysis (PLSA) methods or other collaborative filtering methods are used. Alternatively, the method can apply machine learning clustering algorithms, from less complex methods such as k-means to more complicated approaches such as artificial neural networks (ANN) to perform data clustering. In one embodiment, the method may make use of an ensemble of two or more machine learning methods to achieve better results.

With further reference to FIG. 9, according to another embodiment, the method leverages the resulting clustering data to make recommendations for individual friends (or "buddies") or groups of friends with similar health conditions or preferences, based on comparing user profiles. According to another embodiment, the system will recommend different classes, programs, or events.

Figure 10:
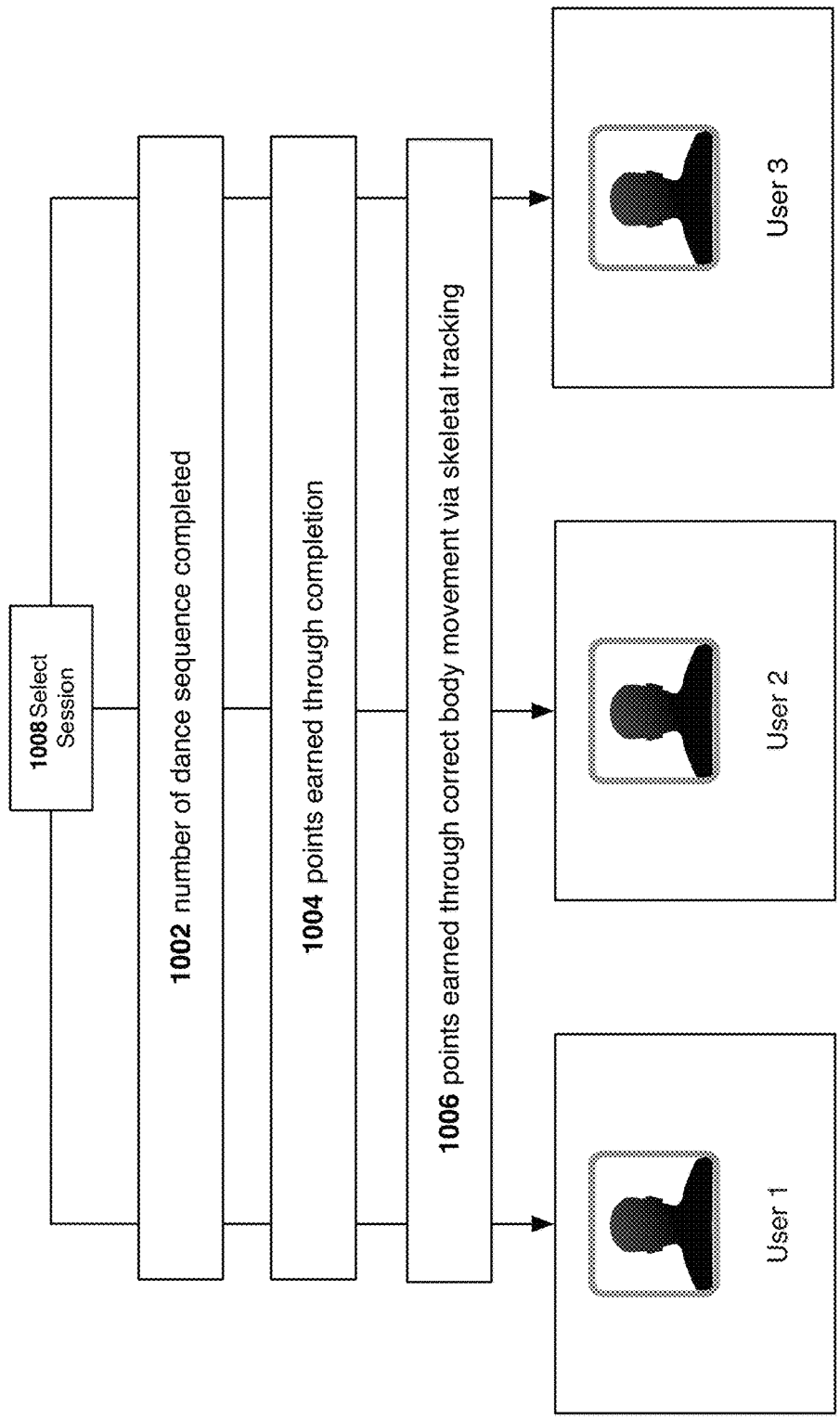
FIG. 10 is a block diagram of a gamification interface according to the principles of the present invention.

FIG. 10 is a block diagram of the gamification interface according to the principles of the present design. According to one, the system includes a gamification interface, whereby after a user select session at operation 1008, data are collected to reflect the user's activity data, such as the number of dance sequences executed per day, points earned by both the completion of the dances at operation 1002, as well as correct body movement confirmed through skeletal tracking at operation 1004 (for example, a user who supposed to exercise her/his shoulder needs to extend her/his arm in the horizontal expansion where her/his hand is at chest height to achieve rotation of her/his rotary cup in her/his shoulder, if her/his hand is below the chest height, she/he is not achieving the therapeutic effect of the dance, if her/his hand is at the correct chest height, s/he will gain a positive score of dance). The users' data are displayed against the scores of "buddies", groups or global users in the system, as derived from the user profile database. The data may also be used to show a user's progress and to compare a user's ability to others to follow a selected dance routine at operation 1006. The descriptions above are exemplary, as the trained observer will recognize that there are a variety of ways different functions may be accomplished, both in hardware and software.

Figure 11:
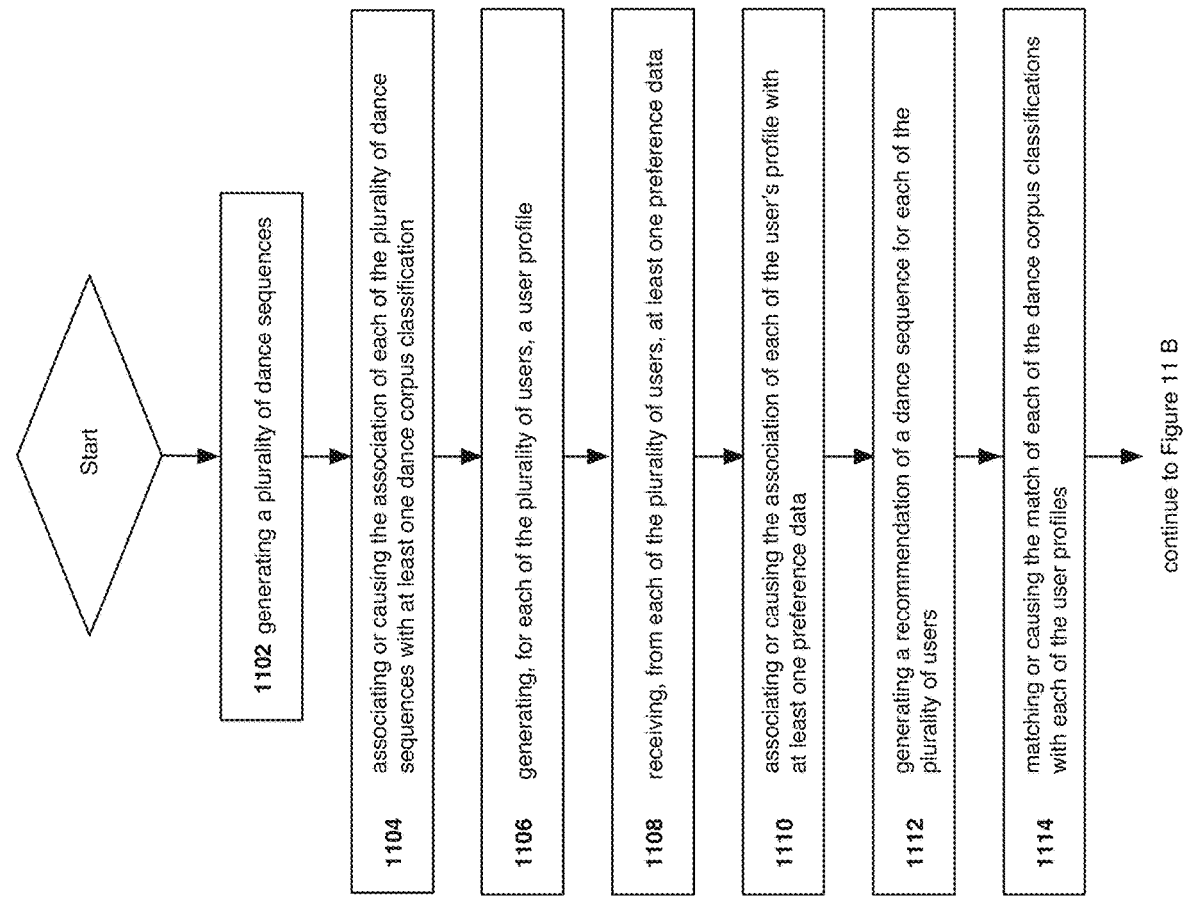
FIGS. 11A and 11B illustrate a method for providing a plurality of users with an environment for personalized dance activities.

The present design can include a system (e.g., system 800, system 1200) to execute a computer-implemented method 1100 of FIGS. 11A and 11B for providing a plurality of users with an environment for personalized dance activities. The computer-implemented method 1100 includes generating a plurality of dance sequences at operation 1102, and associating or causing the association of each of the plurality of dance sequences with at least one dance corpus classification at operation 1104. The computer-implemented method 1100 includes generating, for each of the plurality of users, a user profile at operation 1106 and receiving, from each of the plurality of users, at least one preference data at operation 1108. The computer-implemented method 1100 includes associating or causing the association of each of the user's profile with the at least one preference data at operation 1110 and generating a recommendation of a dance sequence for each of the plurality of users at operation 1112. Generating a recommendation is performed by using collaborative filtering based on the plurality of users' profiles. Generating a recommendation is performed through machine learning techniques for clustering the plurality of dance sequences based on the user profiles and at least one distance metric. The computer-implemented method 1100 further includes matching or causing the match of each of the dance corpus classifications with each of the user profiles at operation 1114. In one example, each user profile includes a mood parameter. The computer-implemented method 1100 further includes tracking at least one movement of each of the plurality of users at operation 1116. Generating a recommendation is performed through evaluating the movement of each of the users. The computer-implemented method 1100 further includes tracking each user's likes and votes at operation 1118. Generating a recommendation is performed through evaluating or causing the evaluation of each user's likes and votes. The computer-implemented method 1100 further includes receiving, from each of the users, at least one other user to dance with at operation 1120. The computer-implemented method 1100 further includes generating a recommendation of at least one other user to dance with for each of the users based on clustering of the respective user-profiles and preferences at operation 1122. The computer-implemented method 1120 further includes displaying or causing the display of recommended dance sequences at operation 1124. Virtual reality or augmented reality devices may be used to consume the dance routine. In one embodiment, a system for providing a plurality of users with an environment for personalized dance activities includes at least one computer including at least one processor (e.g., server 802), the at least one computer in communication with at least one data storage unit (e.g., data storage device 1216 database 804), the at least one computer programmed configured to: generate a plurality of dance sequences; associate or cause the association of each of the plurality of dance sequences with at least one dance corpus classification; generate, for each of the plurality of users, a user profile; receive, from each of the plurality of users, at least one preference data; associate or causing the association of each of the user's profile with the at least one preference data; and generate a recommendation (e.g., recommendation of a dance sequence, recommendation for type of music) for each of the plurality of users.

The present design in one embodiment also includes an interactive interface. This interface includes, in one embodiment, a display that allows the user to select a teacher (based on rating and teacher info), monitor their own progress as well as the progress of friends and groups, determine the type of music and dance they want to perform, watch instructional videos, and evaluate recommendations provided by the system based on user data and feedback.

The present design in another embodiment allows a user to also become a teacher. A user can create and upload their own dance routines and videos and share them with their friends and the entire member community. The member community includes different categories of groups of persons. A user in some embodiments is allowed to join select groups and become a member with other users in the groups as well as anyone in the member community.

The present design in another embodiment allows us to gather online data for teachers who teach music, dance, and art classes online via various live video platforms as well as social media, or in person, creating attributes for the classes they are teaching such as, but not limited to, energy level, the type of music, dance, cultural background, expertise of the teachers, time and location. Upon verification of the effective partnership model created, our system will recommend these as community programs users on our platform can participate. We will also be working with verified partners to train them to record high-quality videos, host these videos on our platform, empower them to convert simple online classes to healthy habit building programs, and recommend these programs tailored specifically to the needs of our users. These needs include, but are not limited to: health history, exercise history, surgery history, energy level, preference of music and dance, preference of gender, cultural background, etc. The system will also track users' feedback, and refine the recommendation based on user feedback, as well as include these feedback data for buddy matching. For example, if the two individuals demonstrate a lot of similarities in their choice of certain types of dance, certain groups of teachers, the system will recommend them as accountable buddies.

The present design in another embodiment will allow us to work with clinical partners to specifically design safety protocols for users with specific health conditions. For example, patients with irregular heartbeat wearing implantable cardioverter-defibrillator (ICD) devices may have anxiety, fear, and PTSD from the shock waves of the device, which reduce their physical activities. The system will utilize biosensor data such as heart rate monitor devices to gather heart rate data continually, provide warning before the participants reach the danger zone of their appropriate heart rates, as well as suggesting appropriate activities that will increase their heart rate when low activity is detected in a safe manner. With enough data gathered, the system can also eventually predict the appropriate level of exercise that may allow users to achieve an ideal heart rate.

The present design in another embodiment uses biosensors, wearable, and other devices to monitor an individual's physiological condition, including stress level, and automatically feeds the data to the environment to adjust the environment according to the person's emotional and physiological state, for example, music, home stereo systems, lighting, environmental controls, etc. The present design collates these data with geolocation data to monitor a population's stress level. These aggregate data can have multiple usages, for example, disaster prediction. It's widely known that animals and humans tend to sense an earthquake before it comes. This information can now be gathered and interpreted in a manner that makes it vital for disaster relief, public health and community health tracking, pandemic progress check and prevention, public safety, crime rate monitoring and reduction, helping first responders know what part of the city they should attend to in the particular time of the day, or during a particular event, etc.

In one embodiment, the present design's biosensor peripheral devices fit into wearables such as fabric or jewelry, such as, but not limited to, an earring, necklace, or a ring is able to tell an individual if they are at risk of, or facing imminent sickness due to exposure to some environmental intruder, either organic or synthetic (bacteria, virus, toxin, gas). A peripheral device, such as a decorative necklace, is enabled to help the wearer know when they are too stressed and prompt a few moments of meditation or other AI-determined programmatic intervention.

In various embodiments of the present design, as described above, an artificial intelligence recommendation system and methods are provided that recommend personalized music and dance based on a users' current physiological and emotional state health condition, reported through a detailed self-assessment and sensor interpolated as well as extrapolated data. The system and methods accomplish these objectives by analyzing databases of patient characteristics, activity history, and databases of music and dance that identify salient physiological and emotional characteristics in order to recommend specific pieces of music and dance to a user, accordingly. Once the music, dance files, patient characteristics, and user preferences have been analyzed and mapped, this system uses an algorithm to provide music and dance recommendations.

In various embodiments of the present design, as described above, the interfaces can be multimodal, including voice, gesture, facial, emotional recognition as well as other modalities. Intelligent wearables such as dance outfits, socks, knee pads, and other types of smart garments can also be used in measuring different activities and impacts, as well as detecting, tutoring, and preventing injuries.

FIG. 12 is a diagram of a computer system including a data processing system according to an embodiment of the invention. Within the computer system 1200 is a set of instructions for causing the machine to perform any one or more of the methodologies discussed herein. In alternative embodiments, the machine may be connected (e.g., networked) to other machines in a LAN, an intranet, an extranet, or the Internet. The machine can operate in the capacity of a server or a client in a client-server network environment, or as a peer machine in a peer-to-peer (or distributed) network environment, the machine can also operate in the capacity of a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

Data processing system 1202 (e.g., CPU 1202), as disclosed above, includes a general-purpose instruction-based processor 1227. The general purpose instruction-based processor may be one or more general-purpose instruction-based processors or processing devices (e.g., microprocessor, central processing unit, or the like). More particularly, data processing system 1202 may be a complex instruction set computing (CISC) microprocessor, reduced instruction set computing (RISC) microprocessor, very long instruction word (VLIW) microprocessor, general-purpose instruction-based processor implementing other instruction sets, or general-purpose instruction-based processors implementing a combination of instruction sets. The in-line accelerator may be one or more special-purpose processing devices such as an application-specific integrated circuit (ASIC), a field-programmable gate array (FPGA), a digital signal general purpose instruction-based processor (DSP), network general-purpose instruction-based processor, many light-weight cores (MLWC) or the like. Data processing system 1202 is configured to implement the data processing system for performing the operations and steps discussed herein.

The exemplary computer system 1200 includes a data processing system 1202, a main memory 1204 (e.g., read-only memory (ROM), flash memory, dynamic random access memory (DRAM) such as synchronous DRAM (SDRAM) or DRAM (RDRAM), etc.), a static memory 1206 (e.g., flash memory, static random access memory (SRAM), etc.), and a data storage device 1216 (e.g., a secondary memory unit in the form of a drive unit, which may include fixed or removable computer-readable storage medium), which communicate with each other via a bus 1208. The storage units disclosed in the computer system 1200 may be configured to implement the data storing mechanisms for performing the operations and steps discussed herein.

The computer system 1200 may further include a network interface device 1222. In an alternative embodiment, the data processing system is integrated into the network interface device 1222 as disclosed herein. The computer system 1200 also may include a video display unit 1210 (e.g., a liquid crystal display (LCD), LED, or a cathode ray tube (CRT)) connected to the computer system through a graphics port and graphics chipset, an input device 1212 (e.g., a keyboard, a mouse), a camera 1214, and a Graphic User Interface (GUI) device 1220 (e.g., a touch-screen with input & output functionality).

The computer system 1200 may further include an RF transceiver 1224 provides frequency shifting, converting received RF signals to baseband and converting baseband transmit signals to RF. In some descriptions a radio transceiver or RF transceiver may be understood to include other signal processing functions such as modulation/demodulation, coding/decoding, interleaving/de-interleaving, spreading/despreading, inverse fast Fourier transforming (IFFT)/fast Fourier transforming (FFT), cyclic prefix appending/removal, and other signal processing functions.

The Data Storage Device 1216 may include a machine-readable storage medium (or more specifically a computer-readable storage medium) on which is stored one or more sets of instructions embodying any one or more of the methodologies or functions described herein. Disclosed data storing mechanisms may be implemented, completely or at least partially, within the main memory 1204 and/or within the data processing system 1202 by the computer system

1200, the main memory 1204 and the data processing system 1202 also constituting machine-readable storage media.

The computer-readable storage medium 1224 may also be used to one or more sets of instructions embodying any one or more of the methodologies or functions described herein. While the computer-readable storage medium 1224 is shown in an exemplary embodiment to be a single medium, the term "computer-readable storage medium" should be taken to include a single medium or multiple media (e.g., a centralized or distributed database, and/or associated caches and servers) that stores the one or more sets of instructions. The terms "computer-readable storage medium" shall also be taken to include any medium that is capable of storing or encoding a set of instructions for execution by the machine and that cause the machine to perform any one or more of the methodologies of the present invention. The term "computer-readable storage medium" shall accordingly be taken to include, but not be limited to, solid-state memories, and optical and magnetic media.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize.

These modifications may be made to the invention in light of the above-detailed description. The terms used in the following claims should not be construed to limit the invention to the specific implementations disclosed in the specification and the claims. Rather, the scope of the invention is to be determined entirely by the following claims, which are to be construed in accordance with established doctrines of claim interpretation.

The invention claimed is:

1. A system for implementing a method for improving physical condition or mood of a subject through personalized dance activity, and for building a subject data base, and for building a subject data set of the system,
    said system comprising:
        at least one computer including at least one processor,
        at least one data storage unit coupled to the at least one processor,
            said data storage unit including:
            the subject data base containing subject data base information and tracking information from the subject,
                wherein said subject data base information comprises unique user identifier information, demographic data, preference data, historical data, lifestyle data, real-time situational data, and real-time mood data, and
                wherein said tracking information comprises facial recognition data from the subject and physiological measurements of the subject from tracking information collection devices and comprising skeletal tracking data, or thermal tracking data, or oxygenation circulatory tracking data,
            the subject data set comprising subject data base information and tracking information from a plurality of users of the system, and
            a repository of live video classes or recorded dance videos, and
        the tracking information collection devices associated with the subject comprising an input device, a camera, and biosensor peripheral device(s) worn by the subject that communicate with the processor, wherein:
        the system initiates and initially builds the subject data base by initially collecting subject data base information and tracking information via the tracking information collection devices from the subject initiating use of the system,
        the system analyzes and interprets the subject data base information and tracking information and makes determinations as to the subject's physiological state and mood and generates from data comprising the subject data base information and the tracking information, the determinations as to the subject's physiological state and mood, the repository of live video classes or recorded dance videos, and the subject data set, a selection of dance routines for the subject,
        the system presents to the subject the selection of dance routines,
        the system accepts from the subject the subject's selected dance routine,
        the system presents to the subject a recorded dance video or live video classes corresponding to the subject's selected dance routine,
        the system collects subject data base information and tracking information via the tracking information collection devices when the subject executes the subject's selected dance routine and engages in the personalized dance activity, and at the conclusion of the subject executing the subject's selected dance routine and engaging in the personalized dance activity,
        the system analyzes and interprets the subject data base information and tracking information from when the subject executes the subject's selected dance routine and engages in the personalized dance activity, and at the conclusion of the subject executing the subject's selected dance routine and engaging in the personalized dance activity, and makes determinations as to the subject's physiological state and mood, whereby the system tracks improvement in the subject's physiological state and mood and refines its ability to generate and present dance routine selections for the subject in each subsequent use by the subject,
        the system builds the subject data set by adding the subject data base information and tracking information to the subject data set, and
        the system continues to build the subject data base and the subject data set with each subsequent use of the system by the subject by collecting subject data base information and tracking information via the tracking information collection devices from each subsequent use of the system by the subject, and adding that subsequent use subject data base information and tracking information to the subject data set.

2. The system of claim 1, wherein the physiological measurements comprise thermal tracking data.

3. The system 1, wherein the physiological measurements comprise skeletal tracking data.

4. The system of claim 1, wherein the physiological measurements comprise oxygenation circulatory tracking data.

5. The system of claim 1, wherein the tracking information comprises triggers or prompts of the subject to dance or continue dancing.

6. The system of claim 1, wherein the tracking information comprises calories burned from dance.

7. The system of claim 1, wherein the historical data includes health condition, type and date of diagnosis of disease, type of treatment or surgery as to the disease, orthopedic or musculoskeletal problems, or exercise habits.

8. The system of claim 1, wherein the lifestyle data comprises sleep data, personality data, romantic activity data, sexual activity data, data as to activities that require neurological executive planning and execution, data as to how often the subject goes to a gym, data on frequency and quality of family contact of the subject, or data on community activities of the subject.

9. The system of claim 1, wherein the tracking information comprises tracking of emotions of the subject before, during and after dance.

10. The system of claim 1, wherein the system comprises subject data base information as to a plurality of subjects, and the subject data set comprises information as to a plurality of users of the computer system.

11. The system of claim 10, wherein in generating the selection of dance routines, the system additionally analyzes the subject data set and matches the subject with at least one buddy who is one of the plurality of users of the system, and presents the at least one buddy to the subject with the selection of dance routines, the system accepts from the subject the subject's selected dance routine and selection of the buddy, and the system presents to the subject and the buddy the subject's selected dance routine, whereby the system provides for the subject and the buddy performing together the subject's selected dance routine.

12. The system of claim 11, wherein the at least one buddy is more than one buddy.

13. The system of claim 11, wherein the system further comprises a gamification interface, wherein data from tracking information collection devices associated with each of the subject and the buddy is analyzed by the system and the system generates a first score based on the number of dance sequences executed per day or points earned by the subject for dance completion or body movement, a second score based on the number of dance sequences executed per day or points earned by the buddy for dance completion or body movement, and a comparison of the first score with the second score, and, communicates to the subject and buddy information comprising the number of dance sequences executed per day or points earned by each of the subject and the buddy and the first score and the second score and the comparison of the first score with the second score.

14. The system of claim 10, wherein the system additionally analyzes the subject data set and matches the subject with a teacher who is one of the plurality of users of the system, and presents the teacher to the subject with the selection of dance routines, the system accepts from the subject the subject's selected dance routine and selection of the teacher, and the system presents to the subject and the teacher the subject's selected dance routine, whereby the system provides for the subject and the teacher performing together the subject's selected dance routine.

15. The system of claim 14, wherein the physiological measurements of the subject and the teacher comprise skeletal tracking data, and the system compares the subject skeletal tracking data and the teacher skeletal tracking data and communicates to the subject whether the subject is matching movement of the teacher for the subject's selected dance routine.

16. A method for improving physical condition or mood of a subject through personalized dance activity, and for building a subject data base, and for building a subject data set comprising providing a subject with the system of claim 1 and the subject has initial use of the system and has at least one subsequent use of the system, wherein, in the initial use of the system,
the system receives subject data base information and tracking information of the subject from the tracking information collection devices and, initiates and initially builds the subject data base from the subject initiating use of the system,
the system analyzes and interprets the subject data base information and tracking information and makes first determinations as to the subject's physiological state and mood and generates from data comprising the subject data base information and the tracking information, the determinations as to the subject's physiological state and mood, the repository of live video classes or recorded dance videos, and the subject data set, a first selection of dance routines for the subject,
the system presents to the subject the first selection of dance routines,
the system accepts from the subject the subject's first selected dance routine,
the system presents to the subject a dance video corresponding to the subject's first selected dance routine,
the system collects subject data base information and tracking information via the tracking information collection devices when the subject executes the subject's first selected dance routine and engages in the personalized dance activity, and at the conclusion of the subject executing the subject's first selected dance routine and engaging in the personalized dance activity,
the system analyzes and interprets the subject data base information and tracking information from when the subject executes the subject's first selected dance routine and engages in the personalized dance activity, and at the conclusion of the subject executing the subject's first selected dance routine and engaging in the personalized dance activity, and makes first determinations as to the subject's physiological state and mood, whereby the system tracks improvement in the subject's physiological state and mood and refines its ability to generate and present dance routine selections for the subject in each subsequent use by the subject,
the system builds the subject data set by adding the subject data base information and tracking information to the subject data set, in each subsequent use of the system,
the system receives subject data base information and tracking information of the subject from the tracking information collection devices and, builds the subject data base from the subject's subsequent use of the system,
the system analyzes and interprets the subject data base information and tracking information and makes determinations as to the subject's physiological state and mood and generates from data comprising the subject data base information and the tracking information, including from the subject's earlier use of the system, the determinations as to the subject's physiological state and mood, the repository of live video classes or dance videos, and the subject data set, a second selection of dance routines for the subject,
the system presents to the subject the second selection of dance routines, the system accepts from the subject the subject's second selected routine, the system presents to the subject a dance video corresponding to the subject's second selected dance routine, the system collects subject data base information and tracking information via the tracking information collection devices when the subject executes the subject's second selected dance routine and engages in the personalized dance activity, and at the conclusion of the subject executing the subject's second selected dance routine and engaging in the personalized dance activity, the system analyzes and interprets the subject data base information and tracking information from when the subject executes the subject's second selected dance routine and engages in the personalized dance activity, and at the conclusion of the subject executing the subject's second selected dance routine and engaging in the personalized dance activity, and from that subject data base information and tracking information and from the subject's earlier use of the system, the system makes determinations as to the subject's physiological state and mood, whereby the system tracks improvement in the subject's physiological state and mood and refines its ability to generate and present dance routine selections for the subject in each subsequent use by the subject, and the system builds the subject data set by adding the subject data base information and tracking information from each subsequent use to the subject data set, whereby there is improving of the physical condition or mood of the subject through personalized dance activity, and there is building of the subject data base, and building of the subject data set.

17. The system of claim 1, wherein the biosensor peripheral device(s) worn by the subject comprises an article of jewelry worn by the subject.

18. The system of claim 1, wherein unique user identifier information comprises the subject's email address or phone number.

19. The system of claim 1, wherein demographic data comprises the subject's age, the subject's gender, the subject's genetics, the subject's ethnicity, the subject's weight, the subject's height, the subject's occupation, the subject's residential city, or the subject's socioeconomic status.

20. The system of claim 1, wherein preference data comprises the subject's privacy preference, the subject's energy level, the subject's favorite music, the subject's favorite dance, the subject's favorite singers, the subject's favorite dancers, the subject's favorite dance teachers, the subject's hobbies or interests, individual(s) or teacher(s) or groups the subject follows, groups the subject participates in, the subject's technical capability, or the subject's availability to dance.

* * * * *